United States Patent [19]
von Weissenfluh

[11] Patent Number: 5,421,725
[45] Date of Patent: Jun. 6, 1995

[54] DEVICE FOR FITTING A MATRIX TO A TOOTH TO BE FILLED

[75] Inventor: Beat von Weissenfluh, Gentilino, Switzerland

[73] Assignee: Hawe-Neos Dental Dr. H. Von Weissenfluh S.A., Bioggio, Switzerland

[21] Appl. No.: 119,675

[22] Filed: Sep. 13, 1993

[30] Foreign Application Priority Data

Oct. 21, 1992 [CH] Switzerland .................. 3266/92

[51] Int. Cl.⁶ .................................... A61C 7/00
[52] U.S. Cl. .................................... 433/149
[58] Field of Search ............................ 433/149

[56] References Cited

U.S. PATENT DOCUMENTS

| | | | |
|---|---|---|---|
| 3,743,226 | 10/1969 | Arlers et al. | 433/149 |
| 3,890,714 | 6/1975 | Gores | 433/149 |
| 4,631,030 | 12/1986 | von Weissenfluh | 433/149 |
| 4,715,816 | 12/1987 | Mogelof | 433/149 |

*Primary Examiner*—Cary E. O'Connor
*Attorney, Agent, or Firm*—Young & Thompson

[57] ABSTRACT

A device for obtaining the fitting of a matrix to a tooth to be filled comprises matrix (5) and wedge (4) or its attachment part (7) made of resin "with memory that is deformable by illumination". The device is made such that when it is illuminated it deforms and pushes matrix (5) to precisely occupy the radicular recess of the tooth to be filled, while when it is not illuminated it again assumes its normal shape. Thus, one obtains a perfect filling that perfectly fits the shape of the tooth.

6 Claims, 2 Drawing Sheets

DEVICE FOR FITTING A MATRIX TO A TOOTH TO BE FILLED

FIELD OF THE INVENTION

The present invention has as its object a device composed of a matrix and a wedge to obtain the fitting of the matrix to the tooth to be filled, a tooth exhibiting an irregular configuration and radicular recess in an approximal zone, characterized in that the matrix and the wedge are made totally of deformable resin or with applied parts made of resin with memory that is essentially deformable by illumination or by heating.

BACKGROUND OF THE INVENTION

There are known difficulties that a dentist encounters in order to make the matrix adhere perfectly to the tooth during filling, particularly the back teeth, when the tooth exhibits in an approximal zone an indentation, in other words the so-called "radicular recess."

Presently transparent matrices are largely used when the filling is done with a resin that can be hardened by illumination. The matrix is normally held in place by a wedge, also transparent, which is illuminated so as to refract the light rays onto the matrix and thereby onto the filling.

However the wedge is incapable of making the matrix adhere perfectly to the tooth when the tooth exhibits an indentation, in other words a radicular recess. This deficiency generally results in an excess of filling material at the approximal cervical level, from where it can be removed only with great difficulty.

SUMMARY OF THE INVENTION

The device according to the invention makes it possible to resolve the problem and is characterized in that the matrix and the wedge or its attachments are made of resin with memory that is essentially deformable through illumination or heating. In the course of the treatment the whole unit, either illuminated or heated in a suitable manner, will be deformed, thus making the matrix adhere perfectly to the shape of the tooth to be filled.

In fact, there have recently appeared on the market some deformable resins "with memory," so to speak, either by illumination or by heating. These resins, under the action of light or heat are deformed and when they are restored to normal light or temperature, they again take on their initial shape, just as though they had remembered it.

The device according to the present invention takes advantage of this important and curious property of these resins.

BRIEF DESCRIPTION OF THE DRAWINGS

With reference to the attached drawings.

DETAILED DESCRIPTION OF THE INVENTION

Figure 1:
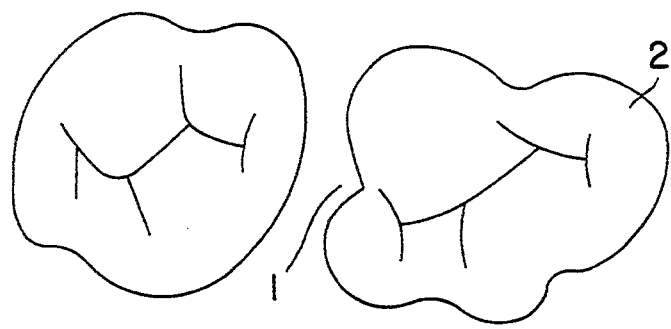
FIG. 1 represents the diagrammatic view of two back molar teeth, of which the one on the right exhibits a radicular recess (indentation) in an approximal zone.

With reference to FIG. 1: of the two molar teeth, in other words back teeth, tooth 2 exhibits the indentation, i.e. radicular recess 1.

During the filling of tooth 2 (FIG. 2), done according to traditional systems, between tooth 2 and adjacent tooth 3 wedge 4 is inserted and presses matrix 5 against the tooth. The matrix surrounds tooth 2 but not perfectly, and thus at the end of the filling process there remains an excess of filling material 6 which is difficult to remove.

Figure 2:
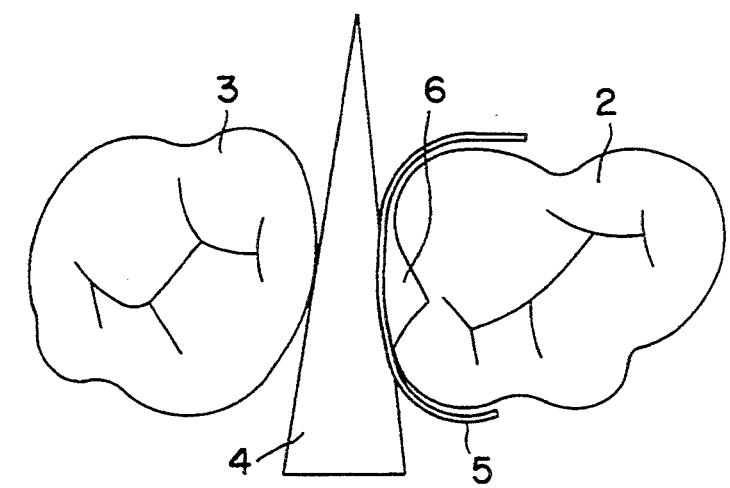
FIG. 2 represents the matrix and the wedge presently used in the filling of a tooth exhibiting the radicular recess and the drawback that results from it.
Figure 3:
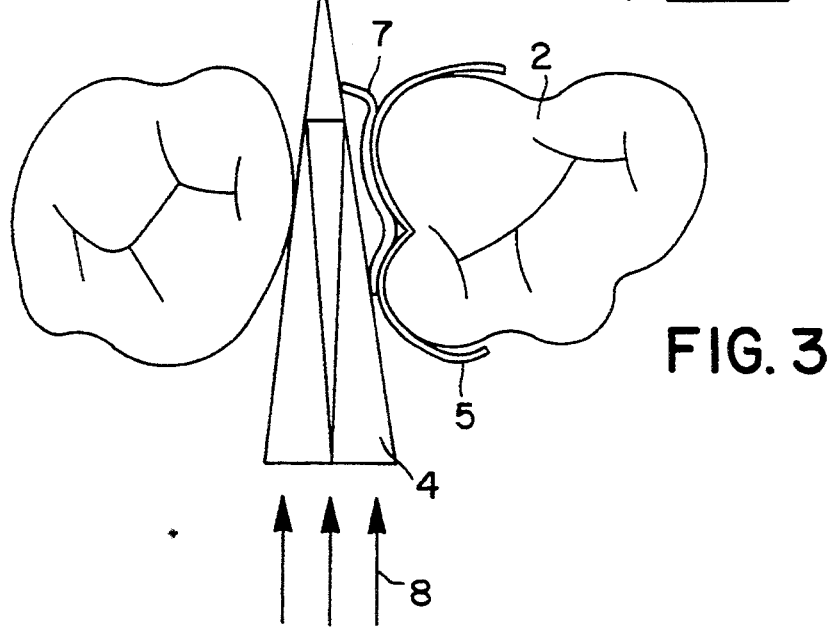
FIGS. 3 to 7 represent various embodiments of the wedge and of the matrix according to the invention, but these are neither limiting nor binding.

Using the device according to the invention (FIG. 3), in contrast, wedge 4 that is transparent is applied to strip or insert 7 made of "deformable resin with memory" and transparent wedge 4 is illuminated with rays 8, matrix 5, that is either transparent or not, is deformed according to the radicular recess, adhering perfectly to the tooth, thus preventing the formation of excess material 6 as illustrated in FIG. 2. In this particular case it is thus sufficient for wedge 4 to be transparent to illuminate strip 7, while matrix 5 can even be non-transparent and the filling can even be composed of amalgam.

If the filling is done with a resin that hardens through illumination, then strip or insert 7 and matrix 4 must also be transparent.

Figure 4:
Figure 5:
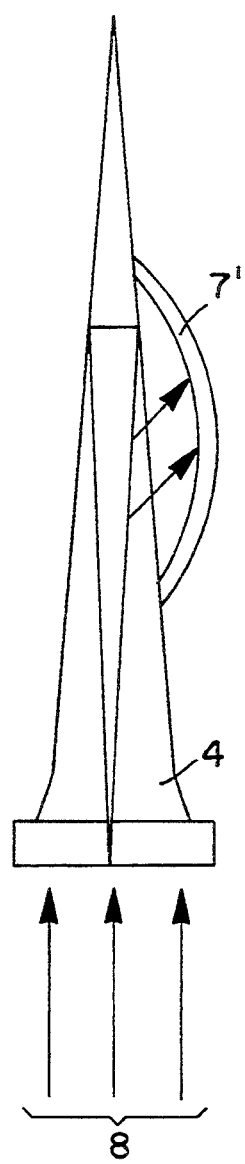
Figure 6:
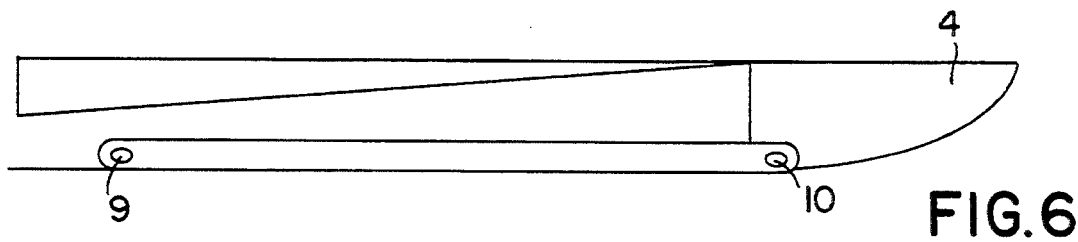
Figure 7:
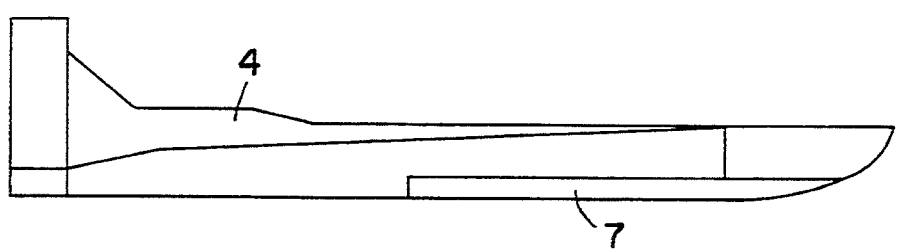

Deformable strip 7 (FIG. 4) can be attached at its two ends A and B to wedge 4 so that it is deformed by the effect of light 8 (FIG. 5) applied to wedge 4 as indicated with 7'. Strip 7 can be attached to wedge 4 with a joint or with rivets 9, 10 (FIG. 6). Wedge 4 can even have a different shape, as illustrated in FIGS. 6 and 7 and strip 7 can be placed in a special housing.

It is clear that if wedge 4 is not illuminated, strip 7 will adhere perfectly to it, withdrawing into its housing, so that it does not impede the insertion of the wedge between teeth.

If deformable strip 7 is a made of a resin that is compatible with that of the wedge, with the known triple injection process the ends of the strip itself can be melted so that it is incorporated with the resin of the wedge, while leaving the central part that is to be deformed in 7' (FIG. 5) free to push matrix 5 (FIG. 2) perfectly within radicular cavity 1 (FIG. 1) of the tooth being filled.

In this case the polymer that composes the strip or the insert must exhibit memory that is "reactive" to light. Practically speaking the insert "with memory" must thus react and change its shape in the space, only if it is illuminated with rays of a determined wave length; this is to prevent the obvious drawbacks of memory determined by "white" light (natural and/or artificial) and to take better advantage of the light originating from the conduction/reflection of wedge 4 in question.

In this way insert 4 can carry out its function of fitting transparent matrix 5 to the edges of the tooth being reconstructed, without impeding and/or disturbing the action of polymerization induced by the light reflected by the wedge, given that the position of the insert (practically along the base of the wedge) and its reduced height cover only a small part of the reflecting zone of the wedge itself.

Figure 8:
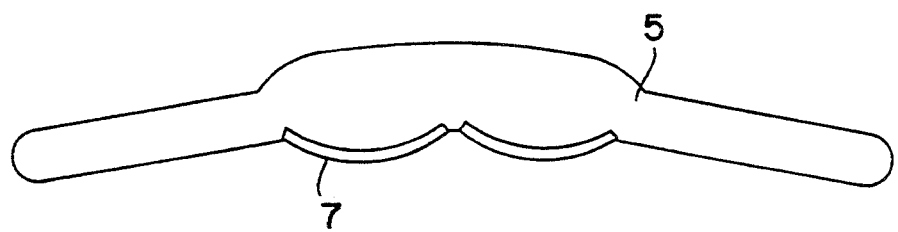
FIG. 8 represents a matrix in distended position, with an insert made of deformable material with memory subjected to illumination.

FIG. 8 represents transparent matrix 5 with insert 7 made of material with memory that is deformable when it is illuminated.

It is obvious that the shape, dimension and the type of resin with memory that make up strip or insert 7, as well as the characteristics of the wedge and of matrix 5 can vary, in a compatible manner with what is claimed in claim 1, without leaving the scope of protection of the patent.

It is even provided that the deformation of the deformable strip or of the wedge with memory can be obtained, besides by illumination, also by the action of heat, although in the case of dentistry this is less advisable.

I claim:

1. Device for obtaining the fitting of a matrix tooth to be filled and exhibiting an irregular configuration and a radicular recess in an approximal zone, said device comprising a matrix and a wedge, said matrix and wedge being totally made of resin with memory that is deformable by one of illumination and heating.

2. Device according to claim 1, further including a strip made of resin with memory that is deformable by one of illumination and heat applied to the matrix and the wedge respectively.

3. Device according to claim 2, wherein said strip has two ends which are attached to the wedge and to the matrix respectively with joint means.

4. Device according to claim 2, wherein said strip has two ends which are incorporated into the resin of the wedge and of the matrix respectively during stamping.

5. Device according to claim 1, wherein the wedge is made of transparent plastic material with resin with memory that is deformable by illumination.

6. Device according to claim 5, wherein the deformable resin with memory reacts to light with a determined wave length, compatible with filling resin.

* * * * *